(12) United States Patent
Wear et al.

(10) Patent No.: US 11,733,144 B2
(45) Date of Patent: Aug. 22, 2023

(54) CONVERTIBLE HOUSING ASSEMBLY FOR A PARTICLE SENSOR

(71) Applicant: Caterpillar Inc., Peoria, IL (US)

(72) Inventors: Daniel Gregory Wear, East Peoria, IL (US); Thomas K. Shim, Edwards, IL (US)

(73) Assignee: Caterpillar Inc., Peoria, IL (US)

( * ) Notice: Subject to any disclaimer, the term of this patent is extended or adjusted under 35 U.S.C. 154(b) by 310 days.

(21) Appl. No.: 17/247,495

(22) Filed: Dec. 14, 2020

(65) Prior Publication Data

US 2022/0187183 A1 Jun. 16, 2022

(51) Int. Cl.
*G01N 15/06* (2006.01)

(52) U.S. Cl.
CPC ..... *G01N 15/06* (2013.01); *G01N 2015/0693* (2013.01)

(58) Field of Classification Search
CPC ........... G01N 15/06; G01N 2015/0693; G01N 2015/0687; G01N 33/2888
See application file for complete search history.

(56) References Cited

U.S. PATENT DOCUMENTS

| 3,906,791 | A | * | 9/1975 | Lynnworth | G01F 1/66 |
| | | | | | 73/861.29 |
| 4,260,258 | A | | 4/1981 | Rose | |
| 4,266,930 | A | * | 5/1981 | Leonard | F24C 3/103 |
| | | | | | 126/41 R |
| 4,547,075 | A | | 10/1985 | Fei | |
| 4,616,927 | A | * | 10/1986 | Phillips | G01N 21/03 |
| | | | | | 356/342 |
| 4,650,094 | A | * | 3/1987 | Werding | B65D 83/7535 |
| | | | | | 239/533.1 |
| 4,886,356 | A | * | 12/1989 | Paradis | G01N 21/05 |
| | | | | | 356/440 |
| 4,940,333 | A | * | 7/1990 | Pawliszyn | G01N 30/74 |
| | | | | | 204/452 |

(Continued)

FOREIGN PATENT DOCUMENTS

| CN | 206020235 U | 3/2017 |
| CN | 110132905 A | 8/2019 |

(Continued)

OTHER PUBLICATIONS

Written Opinion and International Search Report for Int'l. Patent Appln. No. PCT/US2021/062314, dated Mar. 16, 2022 (11 pgs).

*Primary Examiner* — Dominic J Bologna
*Assistant Examiner* — Jarreas C Underwood

(57) ABSTRACT

A convertible housing assembly for a particle sensor includes an integral housing and at least one guide element. The integral housing includes a longitudinal bore, a first intersecting bore, and a second intersecting the bore. The longitudinal bore extends from a first end surface of the integral housing to a second end surface of the integral housing. The first intersecting bore extends from a bottom surface of the integral housing and intersects with the longitudinal bore. The second intersecting bore extends from the bottom surface of the integral housing and intersects with the longitudinal bore. The at least one guide element is secured within the longitudinal bore to reduce turbulence of a fluid flowing therethrough.

20 Claims, 6 Drawing Sheets

(56) References Cited

U.S. PATENT DOCUMENTS

| | | | |
|---|---|---|---|
| 5,404,217 A * | 4/1995 | Janik | G01N 15/1404 |
| | | | 250/576 |
| 5,619,333 A | 4/1997 | Staff et al. | |
| 5,674,397 A | 10/1997 | Pawlak et al. | |
| 6,307,204 B1 * | 10/2001 | Kanomata | G01N 30/74 |
| | | | 250/373 |
| 6,615,872 B2 * | 9/2003 | Goebel | B01F 25/432 |
| | | | 138/37 |
| 6,909,269 B2 | 6/2005 | Nagai et al. | |
| 7,208,123 B2 | 4/2007 | Knollenberg et al. | |
| 7,854,718 B2 | 12/2010 | Gura et al. | |
| 8,597,505 B2 | 12/2013 | Fulkerson et al. | |
| 9,003,895 B2 * | 4/2015 | Laird | F15D 1/025 |
| | | | 73/861.28 |
| 9,989,459 B2 * | 6/2018 | Jeannotte | G01N 21/4133 |
| 10,197,824 B2 * | 2/2019 | Hicks | G01N 21/01 |
| 10,267,723 B1 | 4/2019 | Saaski | |
| 10,772,998 B2 | 9/2020 | Luxon et al. | |
| 10,829,228 B2 * | 11/2020 | Sandiford | F04D 29/547 |
| 2002/0092340 A1 * | 7/2002 | Prater | G02B 7/1821 |
| | | | 73/24.02 |
| 2008/0092888 A1 * | 4/2008 | Haroutunian | F15D 1/001 |
| | | | 128/203.29 |
| 2009/0170149 A1 * | 7/2009 | Viator | G01N 21/1702 |
| | | | 356/73 |
| 2009/0250059 A1 | 10/2009 | Allum | |
| 2010/0315637 A1 * | 12/2010 | Trainoff | G01N 21/51 |
| | | | 356/337 |
| 2014/0338771 A1 * | 11/2014 | Brown | F15D 1/025 |
| | | | 138/40 |
| 2016/0202229 A1 * | 7/2016 | Xiong | G01N 33/18 |
| | | | 73/61.59 |
| 2017/0248572 A1 | 8/2017 | Byington et al. | |
| 2017/0370385 A1 * | 12/2017 | Reckner | G01F 25/10 |
| 2017/0370826 A1 * | 12/2017 | Coombs | G01N 21/0303 |
| 2018/0187234 A1 * | 7/2018 | Kacira | C12Q 1/02 |
| 2019/0317008 A1 | 10/2019 | Schuda | |
| 2019/0383726 A1 * | 12/2019 | Kato | G01N 15/1404 |

FOREIGN PATENT DOCUMENTS

| | | | | |
|---|---|---|---|---|
| CN | 111272236 A | * | 6/2020 | G01F 1/34 |
| WO | 2014043650 A2 | | 3/2014 | |

* cited by examiner

CONVERTIBLE HOUSING ASSEMBLY FOR A PARTICLE SENSOR

TECHNICAL FIELD

The present disclosure relates generally to a particle sensor assembly and, for example, to a convertible housing assembly for a particle sensor.

BACKGROUND

Hydraulic fluid is a key component of many mobile and stationary machines. For example, hydraulic fluid may be used as a lubricant or to facilitate power transfer and/or heat transfer within a system. However, over time, solid particulate may accumulate in hydraulic systems due to ingression of external sources such as dust or sand, or from internal sources such as gear, bearing, or pump wear, which may cause damage or detrimental performance of the systems. To monitor contamination within the hydraulic fluid, some systems may utilize a sensor assembly, which may be cumbersome, expensive, and limited in applicability.

U.S. Pat. No. 4,940,333, which issued to Pawliszyn on Jul. 10, 1990, discloses a detector which measures concentration gradients within a sample. The detector includes a sample chamber, a light source adapted to pass a probe beam of light through the sample chamber, means for detecting the position of the probe beam of light after passing through and leaving the sample chamber, and means for periodically supplying excitation energy to the sample chamber adapted to be absorbed by preselected chemical compounds if present in the chamber. In this way, if the preselected chemical compound is present, it will absorb the excitation energy and create a temperature gradient through photothermal process in the sample that substantially corresponds to the concentration gradient of that chemical in the sample. This temperature gradient will form refractive index gradient and therefore it will also be detected by the probe light beam passing through the sample chamber.

The particle sensor assembly of the present disclosure solves one or more of the problems set forth above and/or other problems in the art.

SUMMARY

In some implementations, a housing for a particle sensor includes a first end surface having a first end opening; a second end surface having a second end opening that communicates with the first end opening to define a longitudinal bore, wherein the second end surface opposes the first end surface; a top surface connecting the first end surface to the second end surface; and a bottom surface having a first bottom opening and a second bottom opening, wherein the first bottom opening communicates with a first intersecting bore that intersects with the longitudinal bore, and the second bottom opening communicates with a second intersecting bore that intersects with the longitudinal bore; wherein the housing is made of single, integral piece of material.

In some implementations, a convertible housing assembly for a particle sensor includes an integral housing comprising: a longitudinal bore that extends from a first end surface of the integral housing to a second end surface of the integral housing; a first intersecting bore that extends from a bottom surface of the integral housing and intersects with the longitudinal bore, and a second intersecting bore that extends from the bottom surface of the integral housing and intersects with the longitudinal bore; and at least one guide element secured within the longitudinal bore to reduce turbulence of a fluid flowing therethrough.

In some implementations, a convertible housing assembly for a particle sensor includes a housing comprising: a longitudinal bore that extends from a first end surface of the housing to a second end surface of the housing, a detection chamber for the particle sensor, wherein the detection chamber extends from a top surface of the housing to a bottom surface of housing and perpendicularly intersects with the longitudinal bore; a first guide element secured within the longitudinal bore at a first side of the detection chamber; and a second guide element secured within the longitudinal bore at a second side of the detection chamber.

DETAILED DESCRIPTION

This disclosure relates to a particle sensor assembly, which is applicable to any system involving a translucent fluid. For example, the fluid may be hydraulic fluid (e.g., mineral oil, water glycol, phosphate ester) or another type of fluid. The system may be implemented in a machine, such as an automobile, a bulldozer, a crane, an excavator, a tractor, or another type of machine.

To simplify the explanation below, the same reference numbers may be used to denote like features. The drawings may not be to scale.

Figure 1:
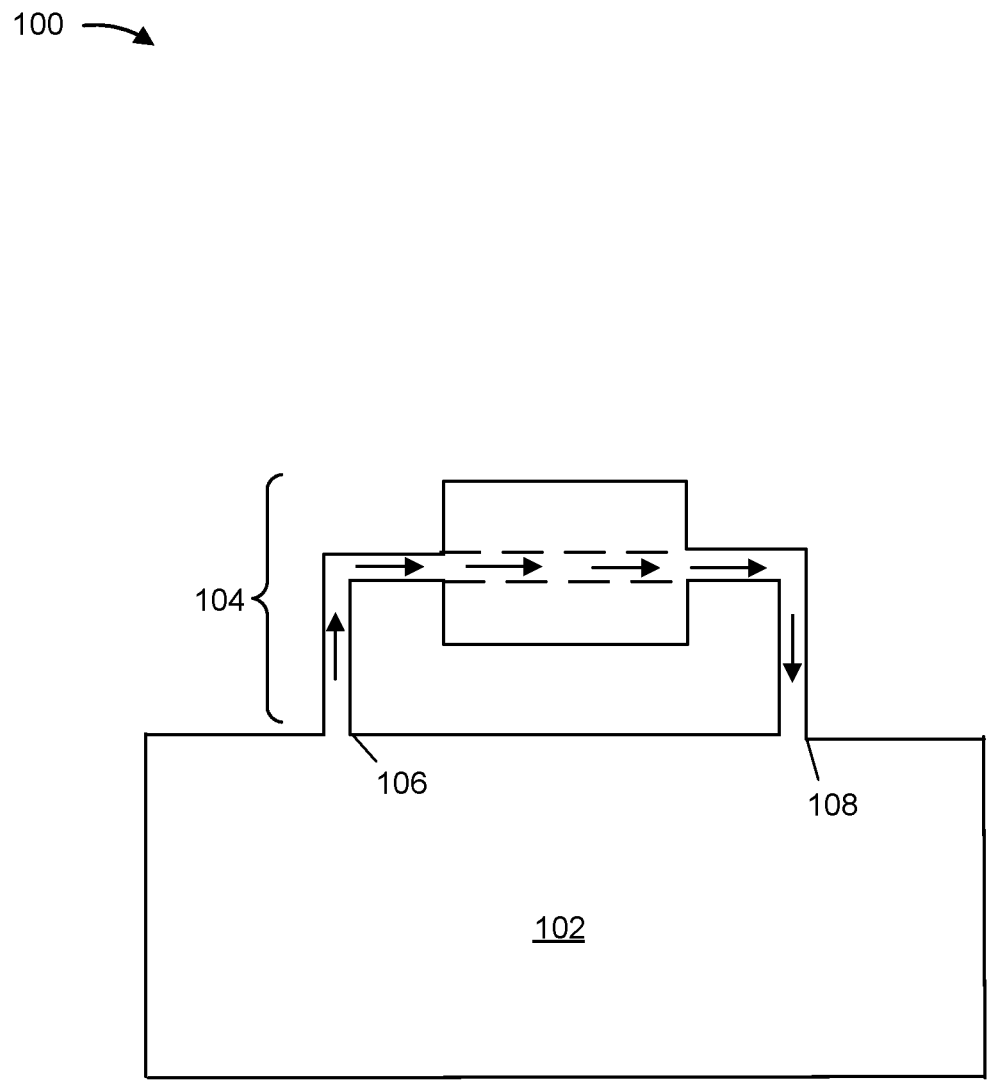
FIG. 1 is a schematic diagram of a fluid monitoring system having a particle sensor assembly.

FIG. 1 is a schematic diagram of a fluid monitoring system 100, which includes a fluid source 102 and a particle sensor assembly 104. The fluid source 102 serves as a source of hydraulic fluid that is to pass through the particle sensor assembly 104. For example, the fluid source 102 may be a reservoir, a pipe, a manifold, a transmission, a filter base, or another type of enclosure having a first hole 106 and a second hole 108. In order to monitor an amount of debris particles (e.g., dust, sand, or other types of particles) therein, the fluid source 102 is attached to the particle sensor assembly 104, which will be described below in connection with FIGS. 2-3. As indicated by the arrows, the hydraulic fluid may pass through the first hole 106 and re-enter the fluid source 102 via the second hole 108 after travelling along a path through the particle sensor assembly 104.

It should be understood that FIG. 1 illustrates a generic flow path of the hydraulic fluid (e.g., out of the fluid source 102, through the particle sensor assembly 104, and back into the fluid source 102) and is not intended to illustrate how the particle sensor assembly 104 is configured and/or attached to the fluid source 102. Depending on space constraints or other factors, the particle sensor assembly 104 may form different configurations, which may alter the shape and/or length of the path. Examples of the different configurations will be described in connection with FIGS. 6-8.

As indicated above, FIG. 1 is provided as an example. Other examples may differ from what is described with regard to FIG. 1. For example, the number and arrangement of components may differ from that shown in FIG. 1. Thus, there may be additional components, fewer components, different components, and/or differently arranged components than those shown in FIG. 1.

Figure 2:
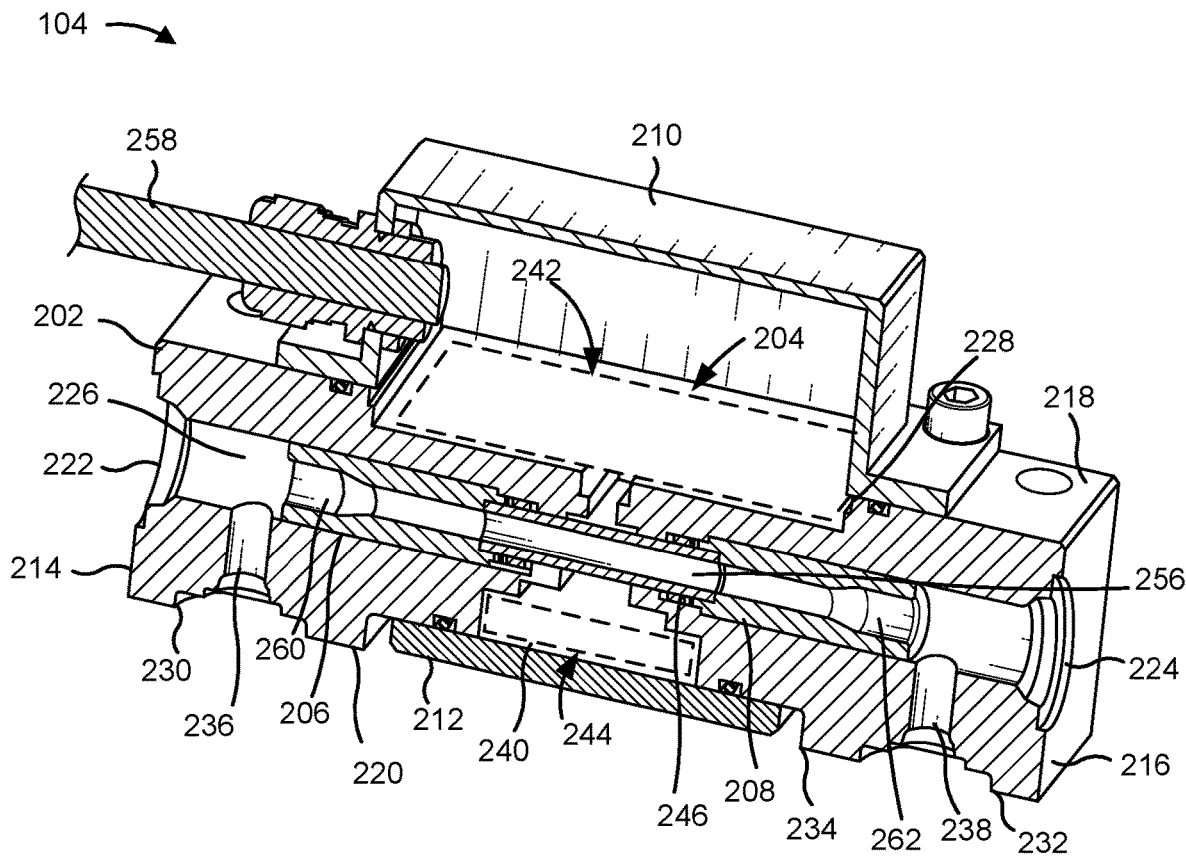
FIG. 2 is a cross-sectional view of the particle sensor assembly.
Figure 3:
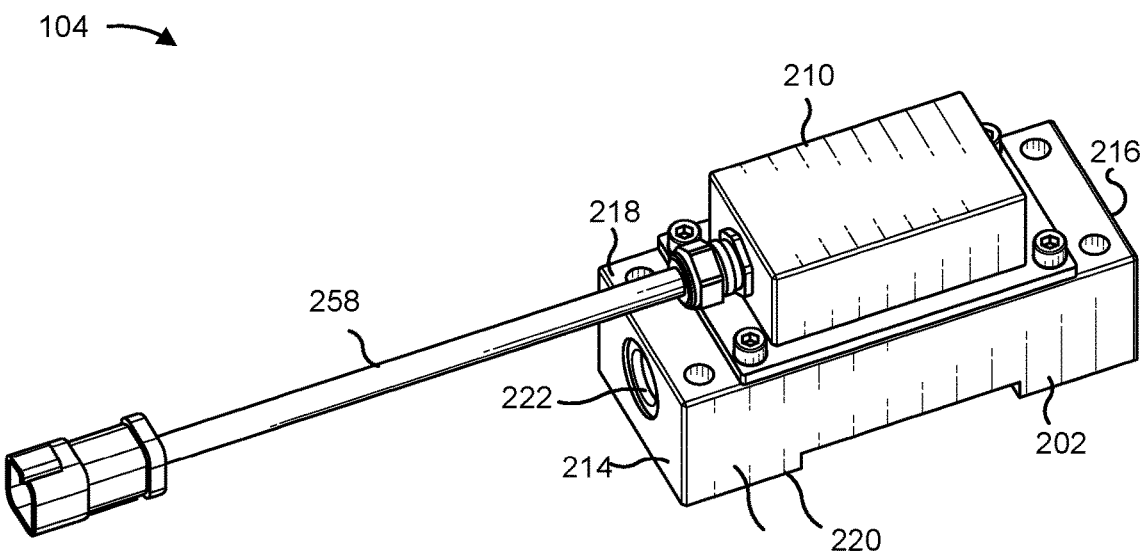
FIG. 3 is an isometric view of the particle sensor assembly.

FIGS. 2-3 are diagrams of the particle sensor assembly 104. FIG. 2 is a cross-sectional view of the particle sensor assembly 104. FIG. 3 is an isometric view of the particle sensor assembly 104.

The particle sensor assembly 104 includes a housing 202, a particle sensor 204, a first guide element 206, a second guide element 208, a cover 210, and a base plate 212. The housing 202, which may be made of a single, integral piece of material (e.g., steel), includes a first end surface 214, a second end surface 216, a top surface 218, and a bottom surface 220. The first end surface 214 includes a first end opening 222. The second end surface 216, which opposes the first end surface 214, includes a second end opening 224 that communicates with the first end opening 222 to define a longitudinal bore 226. The longitudinal bore 226 may be at least partially threaded or otherwise configured to receive the first guide element 206 and the second guide element 208. The top surface 218 connects the first end surface 214 to the second end surface 216 and includes a top opening 228. The bottom surface 220, which opposes the top surface 218, includes a first bottom opening 230, a second bottom opening 232, and a third bottom opening 234. The first bottom opening 230 communicates with a first intersecting bore 236 that intersects with the longitudinal bore 226. The second bottom opening 232 communicates with a second intersecting bore 238 that intersects with the longitudinal bore 226. The third bottom opening 234, which is positioned between the first bottom opening 230 and the second bottom opening 232, communicates with the top opening 228 to define a detection chamber 240 for the particle sensor 204. The detection chamber 240 intersects with the longitudinal bore 226. The first intersecting bore 236, the second intersecting bore 238, and the detection chamber 240 may intersect with the longitudinal bore 226 at an angle of approximately 90 degrees. Other angles of intersection may be possible.

In order to receive one or more modular components, as will be described below in connection with FIGS. 6-8, the first end opening 222, the second end opening 224, the first bottom opening 230, and the second bottom opening 232 may be tapered. For example, one or more of the first end opening 222, the second end opening 224, the first bottom opening 230, and the second bottom opening 232 may form a countersink or a counterbore. Additionally, or alternatively, the first intersecting bore 236 and the second intersecting bore 238 may be at least partially threaded or otherwise configured to receive the one or more modular components. Similarly, the top opening 228 and the third bottom opening 234 may form counterbores to respectively receive components of the particle sensor 204 and the base plate 212.

The particle sensor 204 is an optical sensor that includes a light source 242, a detector 244, and a transparent tube 246 arranged therebetween. The light source 242 may include, for example, a light-emitting diode secured within the top opening 228 of the housing 202. The detector 244 may include, for example, a photodiode situated within the detection chamber 240 to process a pattern of the light passing from the light source 242 through the transparent tube 246. The transparent tube 246, which defines a passage 256 for the hydraulic fluid, is concentrically arranged within the longitudinal bore 226 to extend across the detection chamber 240 and receive the light from the light source 242. The transparent tube 246 may be formed of glass or another type of transparent material. An electric cable 258 may allow the particle sensor 204 to transmit information from the detector 244 to a user interface. Additionally, or alternatively, the electric cable 258 may provide power to the particle sensor 204. Other sources of power, such as a battery and/or a solar panel, may be possible.

The first guide element 206 and the second guide element 208 are concentrically arranged within the longitudinal bore 226 at opposite sides of the transparent tube 246. The first guide element 206 has a first longitudinal bore 260, and the second guide element 208 has a second longitudinal bore 262. The first longitudinal bore 260 and the second longitudinal bore 262 fluidly communicate with the passage 256 of the transparent tube 246 to allow the hydraulic fluid to pass therethrough. As will be described below in connection with FIGS. 3-4, the first guide element 206 and the second guide element 208 are structured and arranged to facilitate transformation of a turbulent flow of the hydraulic fluid into a laminar flow of the hydraulic fluid.

The cover 210 is arranged over the top opening 228 to protect the light source 242 and connect the electric cable 258 to the particle sensor 204. The base plate 212 is secured within the third bottom opening 234 of the bottom surface 220 to protect the detector 244. In other words, the cover 210 and the base plate 212 enclose the particle sensor 204 within the detection chamber 240. The cover 210 and the base plate 212 may be secured to the housing 202 via bolts or other types of fasteners (e.g., screws, clips, and/or the like).

The particle sensor assembly 104, in order to enclose the particle sensor 204, the first guide element 206, and the second guide element 208, has a width in a range of approximately 50 millimeters (mm) to approximately 100 mm, a height in a range of approximately 50 mm to approximately 100 mm, and a length in a range of approximately 100 mm to 200 mm. To secure the first guide element 206, the second guide element 208, and the transparent tube 246 therebetween, the longitudinal bore 226 has a diameter in a range of approximately 12 mm to approximately 15 mm and a length in a range of approximately 100 mm to approximately 200 mm. A diameter of the first intersecting bore 236 and/or the second intersecting bore 238 may be less than or equal to the diameter of the longitudinal bore 226. Other dimensions are contemplated.

As indicated above, FIGS. 2-3 are provided as an example. Other examples may differ from what is described with regard to FIGS. 2-3. For example, the number and arrangement of components may differ from that shown in FIGS. 2-3. Thus, there may be additional components, fewer components, different components, differently shaped components, differently sized components, and/or differently arranged components than those shown in FIGS. 2-3. For example, to simplify production and/or reduce costs, the particle sensor assembly 104 may include only one of the first guide element 206 or the second guide element 208.

Figure 4:
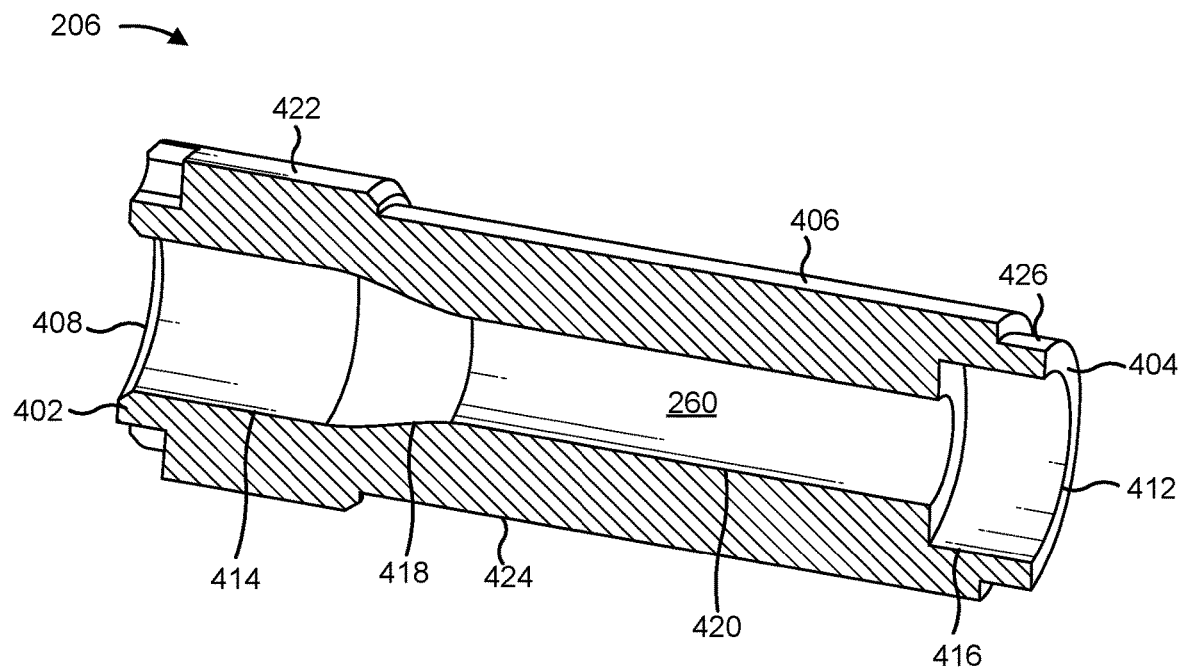
FIG. 4 is a cross-sectional view of a guide element of the particle sensor assembly.
Figure 5:
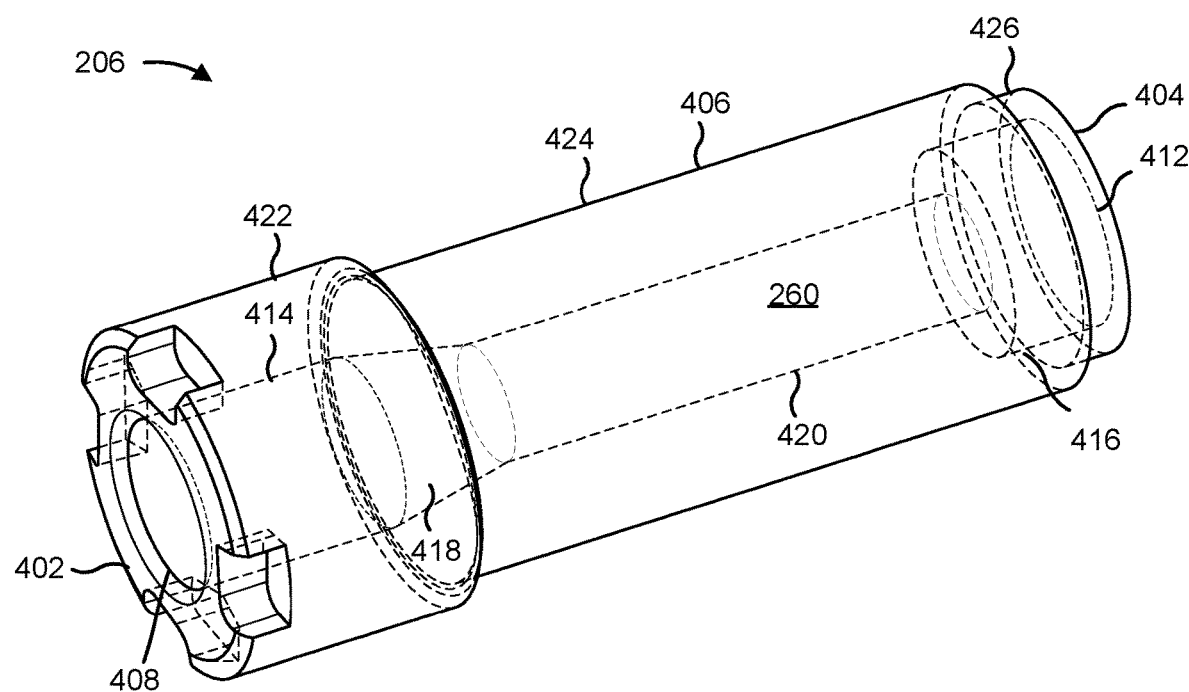
FIG. 5 is an isometric view of the guide element.

FIGS. 4-5 are diagrams of the first guide element 206. FIG. 4 is a cross-sectional view of the first guide element 206. FIG. 5 is an isometric view of the first guide element 206. It should be understood that the first guide element 206 is substantially identical to the second guide element 208 in order to allow the hydraulic fluid to flow in either direction through the longitudinal bore 226.

As shown in FIGS. 4-5, the first guide element 206 includes a first end surface 402, a second end surface 404, and an exterior surface 406 connecting the first end surface 402 to the second end surface 404. The first guide element 206 may be formed from a single, integral piece of material (e.g., steel). The first end surface 402 includes a first opening 408. The first opening 408 may be chamfered to reduce turbulence of the hydraulic fluid passing therethrough. The second end surface 404, which opposes the first end surface 402, includes a second opening 412 that communicates with the first opening 408 to form the first longitudinal bore 260.

The first longitudinal bore 260 includes a first cylindrical section 414, a second cylindrical section 416, a truncated conical section 418, and a third cylindrical section 420. The first cylindrical section 414 is adjacent to the first opening 408, and the second cylindrical section 416 is adjacent to the second opening 412. The truncated conical section 418, which is configured to reduce the turbulence of the hydraulic fluid passing therethrough, is adjacent to the first cylindrical section 414. The third cylindrical section 420 is arranged between the truncated conical section 418 and the second cylindrical section 416. The truncated conical section 418 is tapered such that a diameter of the first cylindrical section 414 is larger than a diameter of the third cylindrical section 420. For example, the diameter of the first cylindrical section 414 may be in a range of approximately 8 mm to approximately 9 mm. The diameter of the third cylindrical section 420 may be in a range of approximately 4 mm to approximately 5 mm. The second cylindrical section 416 is sized to receive an end of the transparent tube 246 (e.g., via a friction fit, clamped between the first guide element 206 and the second guide element 208, or another type of attachment). For example, a diameter of the second cylindrical section 416 may be approximately 8 mm to approximately 9 mm.

Furthermore, the first cylindrical section 414, the second cylindrical section 416, the truncated conical section 418, and the third cylindrical section 420 of the first longitudinal bore 260 have lengths that are configured to ensure that the that the hydraulic fluid enters the transparent tube 246 in a laminar state and with a flow rate in a range of approximately 1.5 liters minute (l/min) to approximately 5 l/min. By ensuring that the hydraulic fluid enters the transparent tube 246 in the laminar state and with the above described flow rate, the first longitudinal bore 260 increases accuracy of the detector 244. For example, the first cylindrical section 414 may have a length in a range of approximately 7 mm to approximately 10 mm. The second cylindrical section 416 may have a length in a range of approximately 5 mm to approximately 7 mm. The truncated conical section 418 may have a length in a range of approximately 4 mm to approximately 7 mm. The third cylindrical section 420 may have a length in a range of approximately 20 to approximately 25 mm.

The exterior surface 406 of the first guide element 206 includes a head portion 422, a shank portion 424, and an end portion 426. In order to threadably secure the first guide element 206 within the longitudinal bore 226, the shank portion 424 may be threaded. The head portion 422 has a diameter that is greater than a diameter of the shank portion 424. For example, the diameter of the head portion 422, which corresponds to a diameter of the first end surface 402, may be in a range of approximately 14 mm to approximately 15 mm. The diameter of the shank portion 424 may be in a range of approximately 12 mm to approximately 14 mm. In order to securely seat the first guide element 206 within the longitudinal bore 226 and against the transparent tube 246, the end portion 426 has a diameter that is less than the diameter of the shank portion 424. For example, the diameter of the end portion 426, which corresponds to a diameter of the second end surface 404, may be in a range of approximately 11 mm to approximately 12 mm. It should be understood that the longitudinal bore 226 has corresponding dimensions.

As indicated above, FIGS. 4-5 are provided as an example. Other examples may differ from what is described with regard to FIGS. 4-5. For example, the number and arrangement of components may differ from that shown in FIGS. 4-5. Thus, there may be additional components, fewer components, different components, differently shaped components, differently sized components, and/or differently arranged components than those shown in FIGS. 4-5. For example, the first guide element 206 and the second guide element 208 (and correspondingly, the housing 202) may be proportionally increased or decreased in size. Thus, as an example and relative to a total length of the first guide element 206, the length of the first cylindrical section 414 may be approximately 20%, the length of the second cylindrical section 416 may be approximately 15%, the length of the truncated conical section 418 may be approximately 12%, and the length of the third cylindrical section 420 may be approximately 53%. As a further example and relative to the diameter of the shank portion 424, the diameter of the first cylindrical section 414 may be approximately 60%, the diameter of the second cylindrical section 416 may be approximately 61%, and the diameter of the third cylindrical section 420 may be approximately 34%. In such an example, the diameter of the truncated conical section 418, relative to the diameter of the shank portion 424, decreases from approximately 60% to approximately 34%.

Figure 6:
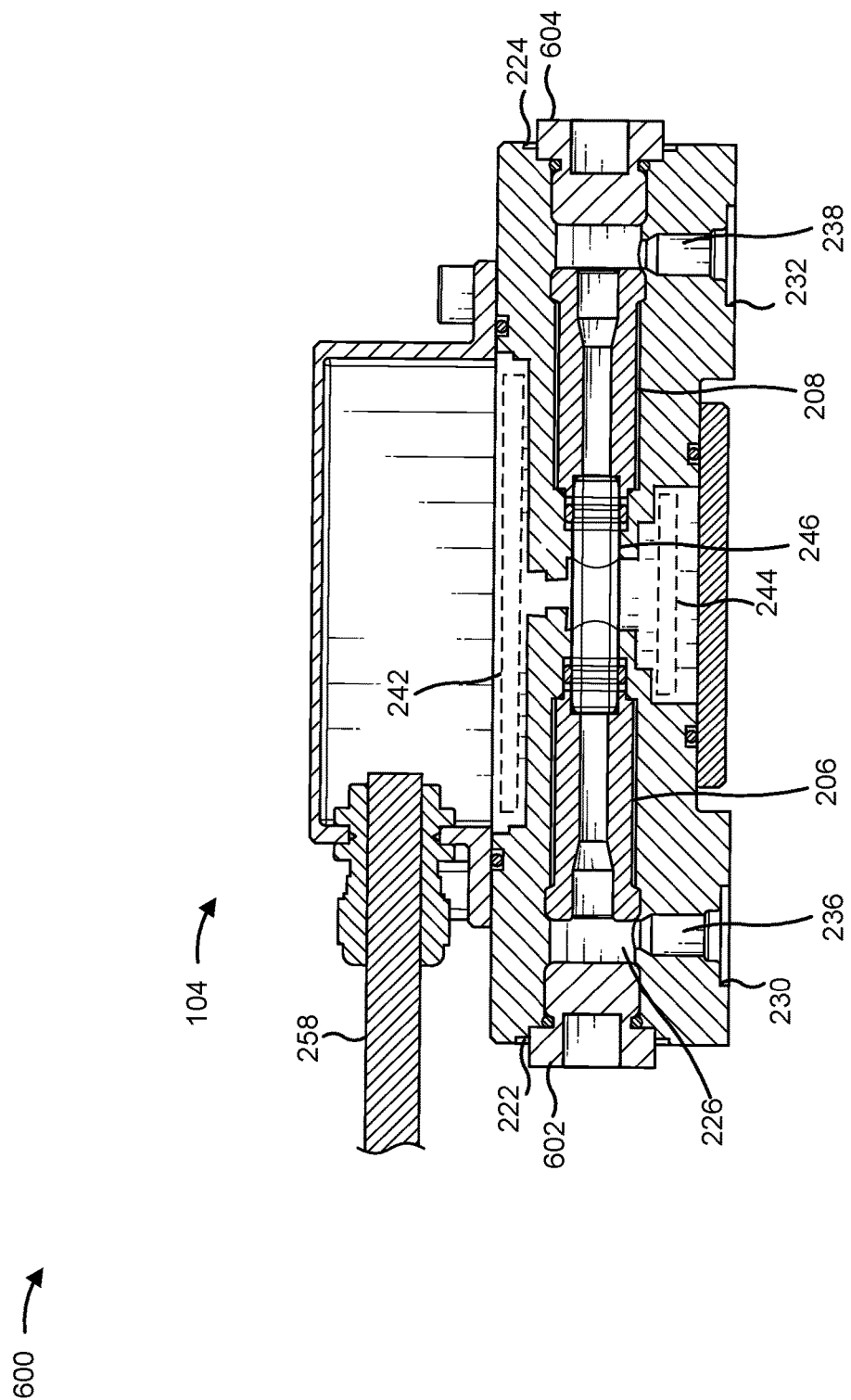
FIG. 6 is a cross-sectional view of the particle sensor assembly in an in-line configuration.
Figure 7:
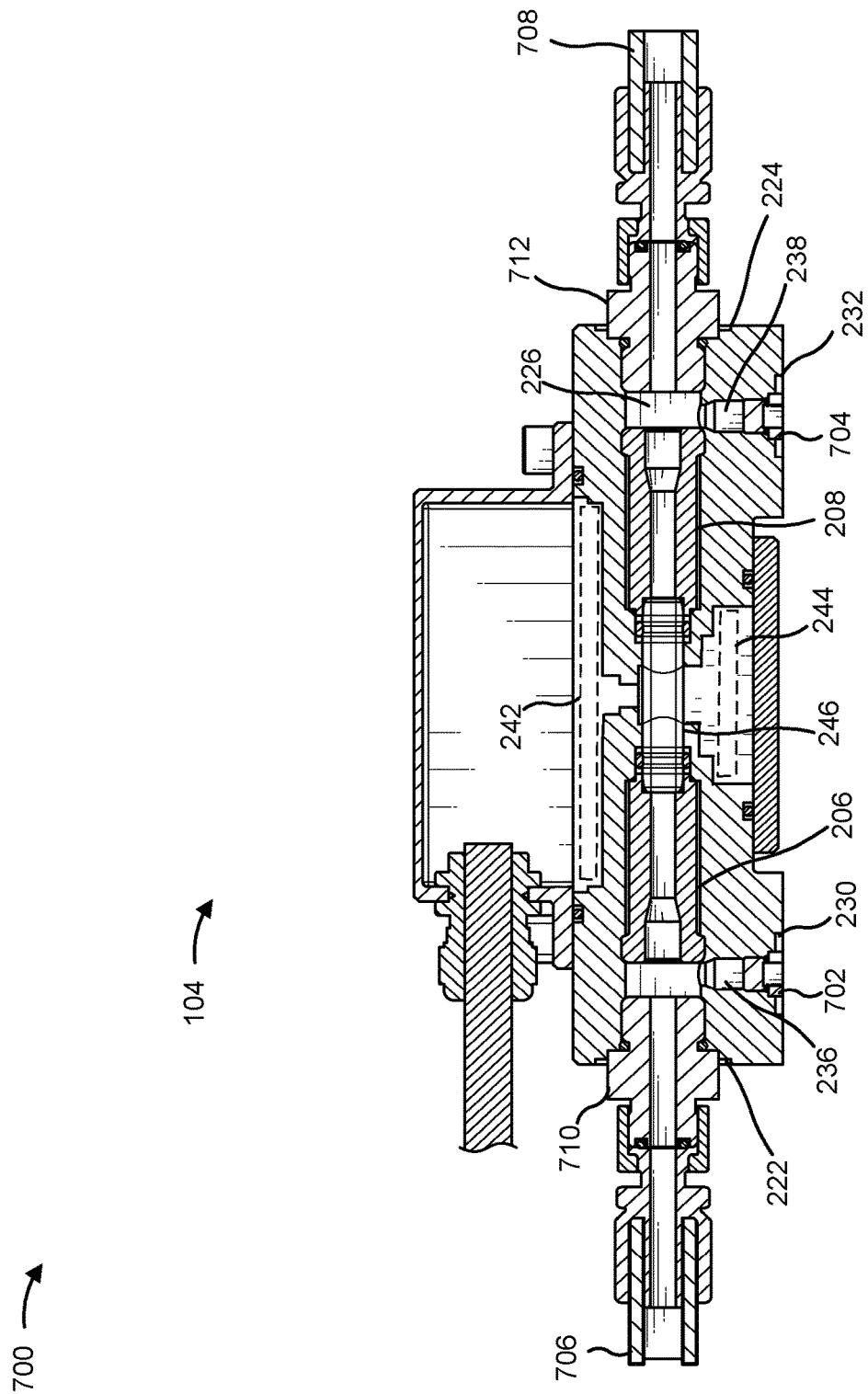
FIG. 7 is a cross-sectional view of the particle sensor assembly in a kidney loop configuration.
Figure 8:
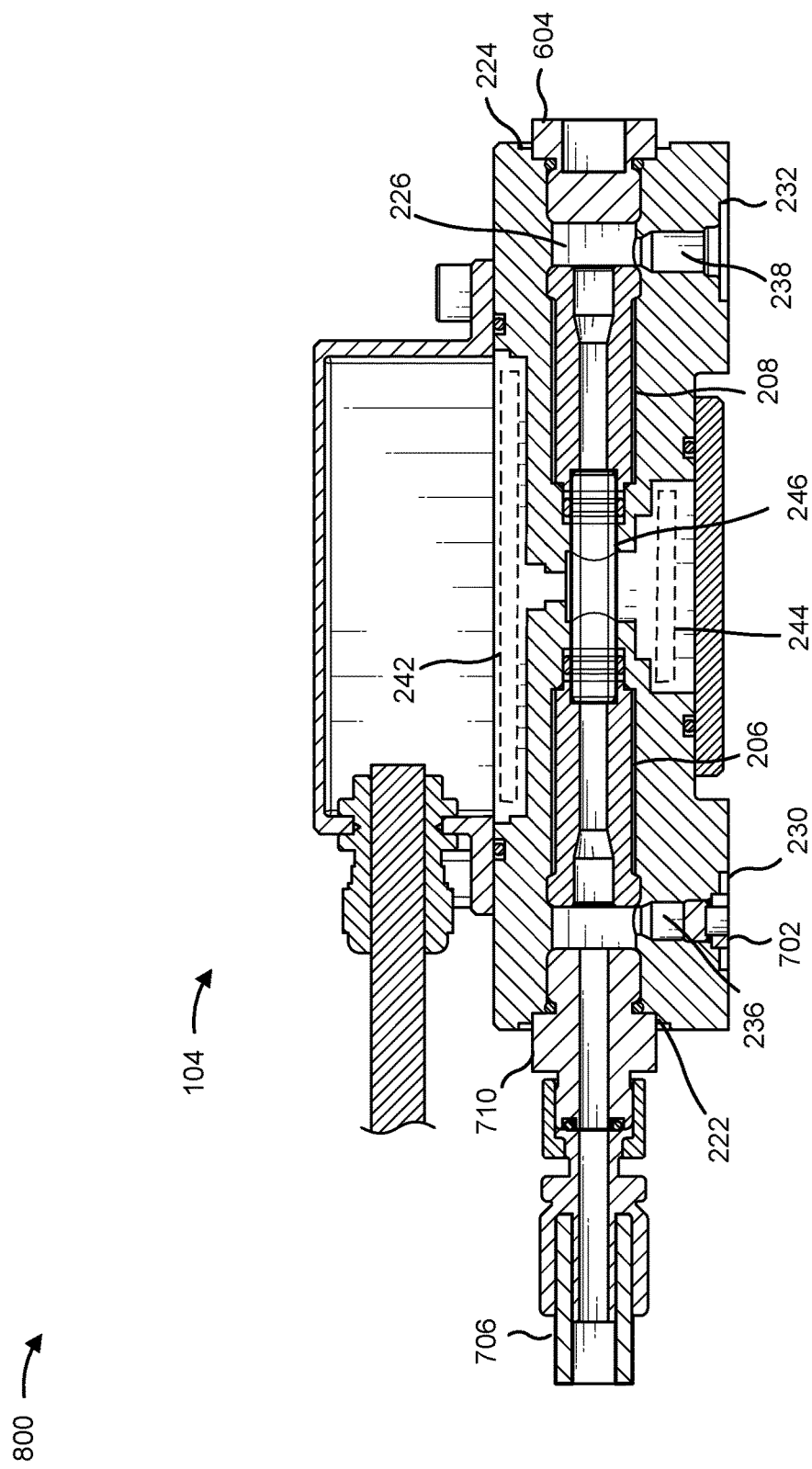
FIG. 8 is a cross-sectional view of the particle sensor assembly in a hybrid configuration.

FIGS. 6-8 are diagrams the particle sensor assembly 104 in different configurations. FIG. 6 is a cross-sectional view of the particle sensor assembly 104 in an in-line configuration 600. FIG. 7 is a cross-sectional view of the particle sensor assembly 104 in a kidney loop configuration 700. FIG. 8 is a cross-sectional view of the particle sensor assembly 104 in a hybrid configuration 800.

As shown in FIG. 6, the in-line configuration 600 of the particle sensor assembly 104 includes a first end plug 602 and a second end plug 604. To limit the path of the hydraulic fluid within the particle sensor assembly 104, the first end plug 602 is removably secured within the first end opening 222 of the longitudinal bore 226, and the second end plug 604 is removably secured within the second end opening 224 of the longitudinal bore 226. For example, the first end plug 602 and the second end plug 604 may be threadably secured within the longitudinal bore 226 or secured via a friction fit attachment, a snap-fit attachment, or another type of attachment.

In use, the particle sensor assembly 104 may be mounted or otherwise secured to the fluid source 102 such that the first bottom opening 230 is aligned with the first hole 106 and the second bottom opening 232 is aligned with the second hole 108. Once the particle sensor assembly 104 is so secured to the fluid source 102, the hydraulic fluid therein may pass along the first intersecting bore 236 to enter the longitudinal bore 226. Due to the change in direction of the flow at the intersection of the first intersecting bore 236 and the longitudinal bore 226, the hydraulic fluid may experience turbulence. As the hydraulic fluid contacts and passes through the first guide element 206, however, the turbulence of the hydraulic fluid may be reduced by the first guide element 206 to render the flow substantially laminar as the hydraulic fluid enters the transparent tube 246. For example, the hydraulic fluid may have a flow rate in a range of approximately 1.5 l/min to approximately 5 l/min as the hydraulic fluid travels through transparent tube 246. Once the light source 242 is illuminated, light passes from the light source 242 through the transparent tube 246 and the hydraulic fluid. Because debris particles within the hydraulic fluid tend to be opaque, the debris particles may cast shadows on the detector 244, which is configured to process the light pattern to determine the amount of debris particles within the hydraulic fluid. The detector 244, via the electric cable 258, may transmit the information to a user interface (e.g., to alert an operator, to cause the hydraulic system to shut down, and/or the like). After the hydraulic fluid exits the transparent tube 246, the hydraulic fluid may travel along the second guide element 208 and the second intersecting bore 238 and re-enter the fluid source 102 via the second hole 108.

As shown in FIG. 7, the kidney loop configuration 700 of the particle sensor assembly 104 includes a first bottom plug 702, a second bottom plug 704, a first hose 706 (shown in part), and a second hose 708 (shown in part). The first hose 706 includes a first hose connector 710 at each end thereof, and the second hose 708 includes a second hose connector 712 at each end thereof. To limit the path of the hydraulic fluid within the particle sensor assembly 104, the first bottom plug 702 is removably secured within the first bottom opening 230 of the first intersecting bore 236, and the second bottom plug 704 is removably secured within the second bottom opening 232 of the second intersecting bore 238. To extend a length of the path of the hydraulic fluid outside of the fluid source 102 (e.g., to dissipate heat, to reduce the flow rate, and/or the like), the first hose 706 is connected to the first end opening 222 of the housing 202 via one of the first hose connectors 710, and the second hose 708 is connected to the second end opening 224 via one of the second hose connectors 712. Similar to the first end plug 602 and the second end plug 604, the first bottom plug 702, the second bottom plug 704, the first hose connectors 710, and the second hose connectors 712 may be threadably secured or secured via a friction fit attachment, a snap-fit attachment, or another type of attachment In use, the particle sensor assembly 104 may be attached to the fluid source 102 such that an opposing one of the first hose connectors 710 is attached to the first hole 106 and an opposing one of the second hose connectors 712 is attached to the second hole 108. Once the particle sensor assembly 104 is so secured to the fluid source 102, the hydraulic fluid therein may travel along the first hose 706, the longitudinal bore 226, and the first guide element 206 to enter the transparent tube 246. The flow rate of the hydraulic fluid passing through the transparent tube 246 may be in range described above. With the light source 242 illuminated, light passes from the light source 242 through the transparent tube 246 and the hydraulic fluid. Because debris particles within the hydraulic fluid tend to be opaque, the debris particles may cast shadows on the detector 244, which is configured to process the light pattern and transmit information associated with the light pattern, as described above. After the hydraulic fluid exits the transparent tube 246, the hydraulic fluid may travel along the second guide element 208 and the second hose 708 and re-enter the fluid source 102 via the second hole 108.

As shown in FIG. 8, the hybrid configuration 800 of the particle sensor assembly 104 is a combination of the in-line configuration 600 and the kidney loop configuration 700. In particular, the hybrid configuration 800 may include a first bottom plug 702, a first hose 706, and a second end plug 604. To limit the path of the hydraulic fluid within the particle sensor assembly 104, the first bottom plug 702 is removably secured within the first bottom opening, and the second end plug 604 is removably secured within the second end opening. To extend a length of the path of the hydraulic fluid outside of the fluid source 102, the first hose 706 is connected to the first end opening 222 of the housing 202 via one of the first hose connectors 710.

In use, the particle sensor assembly 104 may be attached to the fluid source 102 such that an opposing one of the first hose connectors 710 is attached to the first hole 106 and the second bottom opening is aligned with the second hole 108. Once the particle sensor assembly 104 is so secured to the fluid source 102, the hydraulic fluid therein may pass along the first hose 706 and the first guide element 206 to enter the transparent tube 246. As described above, light from the light source 242 passes through the transparent tube 246 and the hydraulic fluid and is processed by the detector 244. After the hydraulic fluid exits the transparent tube 246, the hydraulic fluid may travel along the second guide element 208 and the second intersecting bore 238 and re-enter the fluid source 102 via the second hole 108.

As indicated above, FIGS. 6-8 are provided as an example. Other examples may differ from what is described with regard to FIGS. 6-8. For example, the number and arrangement of components may differ from that shown in FIGS. 6-8. Thus, there may be additional components, fewer components, different components, differently shaped components, differently sized components, and/or differently arranged components than those shown in FIGS. 6-8. For example, the hydraulic fluid may flow in the opposite direction through the particle sensor assembly 104. As a further example, the particle sensor assembly 104 may be unidirectional. In such an example, the second guide element 208 may be eliminated or structurally differ from the first guide element 206 (e.g., by having a non-tapered bore rather than a tapered bore, and/or the like).

INDUSTRIAL APPLICABILITY

The particle sensor assembly 104 of the present disclosure is applicable to any system involving a translucent fluid. For example, the fluid may be hydraulic fluid (e.g., mineral oil, water glycol, phosphate ester) or another type of fluid. The system may be implemented in a machine, such as an automobile, a bulldozer, a crane, an excavator, a tractor, or another type of machine.

Due to the compact size of the particle sensor assembly 104, the particle sensor assembly 104 of the present disclosure has significant benefits in terms of cost effectiveness and versatility in application. Such versatility is further enhanced due to the modularity of the particle sensor assembly 104. For example, depending on space constraints, environmental conditions, and/or other factors, the particle sensor assembly 104 may be secured to the fluid source 102 in the in-line configuration 600, the kidney loop configuration 700, or the hybrid configuration 800. Due to the turbulence-reducing features of the first guide element 206 and/or the second guide element 208 (e.g., the chamfered shape of the first opening 408, the truncated conical section 418, and/or like), the first guide element 206 and/or the second guide element 208 increase the likelihood that the hydraulic fluid enters the transparent tube 246 in a laminar state and at a flow rate in a range of approximately 1.5 l/min to approximately 5 l/min. As a result, the first guide element 206 and/or the second guide element 208 increases accuracy of the detector 244 and may therefore be more effective at protecting the system. Furthermore, the particle sensor assembly 104, due to its modularity, reduces inventory costs associated with ancillary hardware and simplifies installation processes.

The foregoing disclosure provides illustration and description, but is not intended to be exhaustive or to limit the implementations to the precise forms disclosed. Modifications and variations may be made in light of the above disclosure or may be acquired from practice of the implementations. Furthermore, any of the implementations described herein may be combined unless the foregoing disclosure expressly provides a reason that one or more implementations cannot be combined. Even though particular combinations of features are recited in the claims and/or disclosed in the specification, these combinations are not intended to limit the disclosure of various implementations. Although each dependent claim listed below may directly depend on only one claim, the disclosure of various implementations includes each dependent claim in combination with every other claim in the claim set.

As used herein, "a," "an," and a "set" are intended to include one or more items, and may be used interchangeably with "one or more." Further, as used herein, the article "the" is intended to include one or more items referenced in connection with the article "the" and may be used interchangeably with "the one or more." Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of"). Further, spatially relative terms, such as "below," "lower," "above," "upper," and the like, may be used herein for ease of description to describe one element or feature's relationship to another element(s) or feature(s) as illustrated in the figures. The spatially relative terms are intended to encompass different orientations of the apparatus, device, and/or element in use or operation in addition to the orientation depicted in the figures. The apparatus may be otherwise oriented (rotated 90 degrees or at other orientations) and the spatially relative descriptors used herein may likewise be interpreted accordingly.

What is claimed is:

1. A housing for a particle sensor, the housing comprising:
a first end surface having a first end opening;
a second end surface having a second end opening that communicates with the first end opening to define a longitudinal bore,
wherein the second end surface opposes the first end surface,
wherein the longitudinal bore is configured to receive a guide element that includes a single flow path and facilitates transformation of a turbulent flow of a hydraulic fluid into a laminar flow of the hydraulic fluid;
a top surface connecting the first end surface to the second end surface; and
a bottom surface having a first bottom opening and a second bottom opening,
wherein the first bottom opening communicates with a first intersecting bore that intersects with the longitudinal bore, and
wherein the second bottom opening communicates with a second intersecting bore that intersects with the longitudinal bore.

2. The housing of claim 1, wherein
the first intersecting bore intersects with the longitudinal bore at an angle of approximately 90 degrees; and
the second intersecting bore intersects with the longitudinal bore at an angle of approximately 90 degrees.

3. The housing of claim 1, wherein the longitudinal bore, the first intersecting bore, and the second intersecting bore are at least partially threaded.

4. The housing of claim 1, wherein the first end opening, the second end opening, the first bottom opening, and the second bottom opening are tapered.

5. The housing of claim 1, wherein
the longitudinal bore has a diameter in a range of approximately 12 millimeters to approximately 15 millimeters; and
the longitudinal bore has a length in a range of approximately 100 millimeters to approximately 200 millimeters.

6. The housing of claim 1 wherein
the top surface comprises a top opening; and
the bottom surface further comprises a third bottom opening that communicates with the top opening to define a detection chamber for the particle sensor,
wherein the detection chamber intersects with the longitudinal bore.

7. A convertible housing assembly for a particle sensor, the convertible housing assembly comprising:
an integral housing comprising:
a longitudinal bore that extends from a first end surface of the integral housing to a second end surface of the integral housing;
a first intersecting bore that extends from a bottom surface of the integral housing and intersects with the longitudinal bore, and
a second intersecting bore that extends from the bottom surface of the integral housing and intersects with the longitudinal bore; and
at least one guide element secured within the longitudinal bore to transform a turbulent flow of a fluid into a laminar flow of the fluid,
the at least one guide element including a single flow path.

8. The convertible housing assembly of claim 7, further comprising:
a first end plug secured to the longitudinal bore at the first end surface of the integral housing; and
a second end plug secured to the longitudinal bore at the second end surface of the integral housing,
wherein the first end plug and the second end plug restrict flow of the fluid within the integral housing to between the first intersecting bore, a portion of the longitudinal bore, and the second intersecting bore.

9. The convertible housing assembly of claim 7, further comprising:
a first hose connector secured to the longitudinal bore at the first end surface of the integral housing;
a second hose connector secured to the longitudinal bore at the second end surface of the integral housing;
a first bottom plug secured to the first intersecting bore at the bottom surface of the integral housing; and
a second bottom plug secured to the second intersecting bore at the bottom surface of the integral housing,
wherein the first bottom plug and the second bottom plug restrict flow of the fluid within the integral housing to the longitudinal bore.

10. The convertible housing assembly of claim 7, further comprising:

a first hose connector secured to the longitudinal bore at the first end surface of the integral housing;

a second end plug secured to the longitudinal bore at the second end surface of the integral housing; and a first bottom plug secured to the first intersecting bore at the bottom surface of the integral housing, wherein the second end plug and the first bottom plug restrict flow of the fluid within the integral housing to between a portion of the longitudinal bore and the second intersecting bore.

11. The convertible housing assembly of claim 7, further comprising a detection chamber for the particle sensor, wherein the detection chamber extends from a top surface of the integral housing to the bottom surface of the integral housing and intersects with the longitudinal bore.

12. The convertible housing assembly of claim 11, further comprising:

a cover secured to the top surface of the integral housing that covers a top end of the detection chamber; and a base plate secured to the bottom surface of the integral housing that covers a bottom end of the detection chamber.

13. The convertible housing assembly of claim 7, wherein the at least one guide element includes two substantially identical guide elements that provide the single flow path.

14. The convertible housing assembly of claim 7, wherein the convertible housing assembly has a width in a first range of approximately 50 millimeters to approximately 100 millimeters;

a height in a second range of approximately 50 millimeters to approximately 100 millimeters; and a length in a third range of approximately 100 millimeters to approximately 200 millimeters.

15. A convertible housing assembly for a particle sensor, the convertible housing assembly comprising:

a housing comprising:

a longitudinal bore that extends from a first end surface of the housing to a second end surface of the housing, a detection chamber for the particle sensor, wherein the detection chamber extends from a top surface of the housing to a bottom surface of housing and perpendicularly intersects with the longitudinal bore;

a first guide element secured within the longitudinal bore at a first side of the detection chamber; and a second guide element secured within the longitudinal bore at a second side of the detection chamber, wherein the first guide element and the second guide element include a single flow path and facilitate transformation of a turbulent flow of a fluid into a laminar flow of the fluid.

16. The convertible housing assembly of claim 15, wherein at least one of the first guide element or the second guide element includes a tapered bore to reduce turbulence of the fluid.

17. The convertible housing assembly of claim 15, wherein the longitudinal bore includes:

a first end plug threadably secured at the first end surface, and a second end plug threadably secured at the second end surface; and the housing further includes:

a first intersecting bore that extends from the bottom surface of the housing and intersects with the longitudinal bore, and a second intersecting bore that extends from the bottom surface of the housing and intersects with the longitudinal bore.

18. The convertible housing assembly of claim 15, wherein the longitudinal bore includes:

a first hose connector threadably secured at the first end surface, and a second hose connector threadably secured at the second end surface; and the housing further includes:

a first intersecting bore that extends from the bottom surface of the housing and intersects with the longitudinal bore, wherein the first intersecting bore includes a first bottom plug threadably secured therein, and a second intersecting bore that extends from the bottom surface of the housing and intersects with the longitudinal bore, wherein the second intersecting bore includes a second bottom plug threadably secured therein.

19. The convertible housing assembly of claim 15, wherein the longitudinal bore includes:

a first hose connector threadably secured at the first end surface, and a second end plug threadably secured at the second end surface; and the housing further includes:

a first intersecting bore that extends from the bottom surface of the housing and intersects with the longitudinal bore, wherein the first intersecting bore includes a first bottom plug threadably secured therein, and a second intersecting bore that extends from the bottom surface of the housing and intersects with the longitudinal bore.

20. The convertible housing assembly of claim 15, further comprising:

a cover secured to the top surface of the housing that covers a top end of the detection chamber; and a base plate secured to the bottom surface of the housing that covers a bottom end of the detection chamber.

* * * * *